(12) United States Patent
Jenkins et al.

(10) Patent No.: US 11,786,750 B2
(45) Date of Patent: Oct. 17, 2023

(54) MODULATING NEURAL ACTIVITY IN BRAINSTEM CIRCUITRY WITH LIGHT

(71) Applicants: CASE WESTERN RESERVE UNIVERSITY, Cleveland, OH (US); VANDERBILT UNIVERSITY, Nashville, TN (US)

(72) Inventors: Michael W. Jenkins, Cleveland, OH (US); Stephen J. Lewis, Cleveland, OH (US); Hillel J. Chiel, Cleveland, OH (US); Eric Duco Jansen, Cleveland, OH (US); Junqi Zhuo, Cleveland, OH (US); Emilie Lothet, Cleveland, OH (US); Gjinovefa Kola, Cleveland, OH (US)

(73) Assignees: CASE WESTERN RESERVE UNIVERSITY, Cleveland, OH (US); VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 16/767,277

(22) PCT Filed: Nov. 30, 2018

(86) PCT No.: PCT/US2018/063426
§ 371 (c)(1),
(2) Date: May 27, 2020

(87) PCT Pub. No.: WO2019/109008
PCT Pub. Date: Jun. 6, 2019

(65) Prior Publication Data
US 2020/0406057 A1    Dec. 31, 2020

Related U.S. Application Data

(60) Provisional application No. 62/592,634, filed on Nov. 30, 2017.

(51) Int. Cl.
*A61N 5/06* (2006.01)
*A61N 5/067* (2006.01)

(52) U.S. Cl.
CPC ......... *A61N 5/0622* (2013.01); *A61N 5/0601* (2013.01); *A61N 5/067* (2021.08);
(Continued)

(58) Field of Classification Search
CPC ............... A61N 5/0622; A61N 5/0601; A61N 2005/0626; A61N 2005/0659; A61N 2005/067; A61N 2005/0612
See application file for complete search history.

(56) References Cited

U.S. PATENT DOCUMENTS

| | | | |
|---|---|---|---|
| 2010/0292758 A1* | 11/2010 | Lee | A61N 5/0601 607/55 |
| 2011/0295331 A1* | 12/2011 | Wells | A61N 1/0541 607/3 |
| 2017/0189712 A1* | 7/2017 | Lippert | A61N 5/0622 |

OTHER PUBLICATIONS

Wang X, Piñol RA, Byrne P, Mendelowitz D. Optogenetic stimulation of locus ceruleus neurons augments inhibitory transmission to parasympathetic cardiac vagal neurons via activation of brainstem α1 and β1 receptors. J Neurosci. Apr. 30, 2014;34(18):6182-9. (Year: 2014).*

(Continued)

*Primary Examiner* — Lynsey C Eiseman
*Assistant Examiner* — Ranjani Mari Sundaresan
(74) *Attorney, Agent, or Firm* — TAROLLI, SUNDHEIM, COVELL & TUMMINO, LLP (57) ABSTRACT

The present disclosure relates to modulating neural activity within brainstem circuitry to evoke a certain bodily function (e.g., cardiorespiratory response) in a patient. A controller can configure a light signal (such as an infrared light signal) to deliver an amount of radiant exposure to a specific portion of the brainstem for a time. The specific portion of the (Continued)

brainstem can include brainstem circuitry that is the control center for the certain bodily function. The configured light signal can be delivered to the specific portion of the brainstem by an optrode for the time. During application, the light signal can deliver the amount of radiant exposure to the specific portion of the brainstem to evoke the certain bodily function.

16 Claims, 11 Drawing Sheets

(52) U.S. Cl.
CPC ............. *A61N 2005/0626* (2013.01); *A61N 2005/0659* (2013.01)

(56) References Cited

OTHER PUBLICATIONS

Yamamoto et al., Acute intermittent optogenetic stimulation of nucleus tractus solitarius induces sympathetic long-term facilitation, vol. 308, Issue 4, Feb. 2015, pp. R266-R275 (Year: 2015).*
Thompson et al. Optical Stimulation of Neurons. Curr Mol Imaging. 2014;3(2):162-177 (Year: 2014).*
Lopes LT, Patrone LG, Li KY, Imber AN, Graham CD, Gargaglioni LH, Putnam RW. Anatomical and functional connections between the locus coeruleus and the nucleus tractus solitarius in neonatal rats. Neuroscience. Jun. 2, 2016;324:446-68. doi: 10.1016/j.neuroscience.2016.03.036. Epub Mar. 19, 2016. PMID: 2 (Year: 2016).*
Wells J, Kao C, Konrad P, Milner T, Kim J, Mahadevan-Jansen A, Jansen ED. Biophysical mechanisms of transient optical stimulation of peripheral nerve. Biophys J. Oct. 1, 2007;93(7):2567-80. doi: 10.1529/biophysj.107.104786. Epub May 25, 2007. PMID: 17526565; PMCID: PMC1965456.
Albert, Sylvan J., and Jurg Kesselring. "Neurorehabilitation of stroke." Journal of neurology 259.5 (2012): 817-832.
Bec JM, Albert ES, Marc I, Desmadryl G, Travo C, Muller A, Chabbert C, Bardin F, Dumas M. Characteristics of laser stimulation by near infrared pulses of retinal and vestibular primary neurons. Lasers Surg Med. Nov. 2012;44 (9):736-45. doi: 10.1002/lsm. 22078. Epub Sep. 27, 2012. PMID: 23018648.
Yao J, Liu B, Qin F. Rapid temperature jump by infrared diode laser irradiation for patch-clamp studies. Biophys J. May 6, 2009;96(9):3611-9. doi: 10.1016/j.bpj.2009.02.016. PMID: 19413966; PMCID: PMC2711624.
Shapiro MG, Homma K, Villarreal S, Richter CP, Bezanilla F. Infrared light excites cells by changing their electrical capacitance. Nat Commun. Mar. 13, 2012;3:736. doi: 10.1038/ncomms1742. Erratum in: Nat Commun. Nov. 10, 2017;8:16148. PMID: 22415827; PMCID: PMC3316879.
Liu S, Chistol G, Bustamante C. Mechanical operation and intersubunit coordination of ring-shaped molecular motors: insights from single-molecule studies. Biophys J. May 6, 2014;106(9):1844-58. doi: 10.1016/j.bpj.2014.03.029. PMID: 24806916; PMCID: PMC4017299.
Teudt IU, Maier H, Richter CP, Kral A. Acoustic events and "optophonic" cochlear responses induced by pulsed near-infrared laser. IEEE Trans Biomed Eng. Jun. 2011;58(6):1648-55. doi: 10.1109/TBME.2011.2108297. Epub Jan. 28, 2011. PMID: 21278011; PMCID: PMC3449328.
Dittami GM, Rajguru SM, Lasher RA, Hitchcock RW, Rabbitt RD. Intracellular calcium transients evoked by pulsed infrared radiation in neonatal cardiomyocytes. J Physiol. Mar. 15, 2011;589(Pt 6):1295-306. doi: 10.1113/physiol.2010.198804. Epub Jan. 17, 2011. PMID: 21242257; PMCID: PMC3082093.
Cayce JM, Friedman RM, Chen G, Jansen ED, Mahadevan-Jansen A, Roe AW. Infrared neural stimulation of primary visual cortex in non-human primates. Neuroimage. Jan. 1, 2014;84:181-90. doi: 10.1016/j.neuroimage.2013.08.040. Epub Aug. 28, 2013. PMID: 23994125; PMCID: PMC4120263.
PCT International Search Report and Written Opinion for corresponding International Application Serial No. PCT/US2018/063426, dated Feb. 12, 2019, pp. 1-12.
Abbott, Stephen BG, et al. "Photostimulation of retrotrapezoid nucleus phox2b-expressing neurons in vivo produces long-lasting activation of breathing in rats." Journal of Neuroscience 29.18 (2009): 5806-5819.
European Office Action for corresponding European Application Serial No. 18821886.1, dated Oct. 19, 2021, pp. 1-5.

* cited by examiner

FIG. 12

MODULATING NEURAL ACTIVITY IN BRAINSTEM CIRCUITRY WITH LIGHT

RELATED APPLICATION

This application claims priority to U.S. Provisional Application Ser. No. 62/592,634, filed Nov. 30, 2017, entitled "INFRARED MODULATION OF BRAINSTEM CIRCUITRY", the entirety of which is hereby incorporated by reference for all purposes.

GOVERNMENT FUNDING

This invention was made with government support under NS087249, EB021772, HL126747, HL115373, and OD016236 awarded by the National Institutes of Health; and 1065489 awarded by the National Science Foundation. The government has certain rights in the invention.

TECHNICAL FIELD

The present disclosure relates generally to neural modulation and, more specifically, to systems and methods for using light to modulate neural activity in brainstem circuitry.

BACKGROUND

The control center of basic bodily functions (e.g., breathing, swallowing, heart rate, blood pressure, consciousness, and wakefulness), generation of motor patterns, and sensory integration is located in the brainstem. The control center is implemented as brainstem circuitry, including groups of neurons that perform the control tasks. The brainstem is an accessible, yet underutilized, target for neural modulation within the brain. Such underutilization is due to the fact that traditional neuromodulatory stimuli, like electrical stimuli and magnetic stimuli, are not selective for a certain space within the brainstem being stimulated. Accordingly, electrical stimuli and magnetic stimuli have a high risk of modulating the function of unintended brainstem circuitry, thereby affecting unintended bodily functions.

SUMMARY

The present disclosure relates generally to neural modulation and, more specifically, to systems and methods for using light to modulate neural activity in brainstem circuitry. Neural modulation with light provides a high spatial selectivity and level of precision not seen with traditional electrical and magnetic stimuli.

In an aspect, the present disclosure can include a method for neural modulation of a certain area of a patient's brainstem to evoke a cardiorespiratory response. The method can include configuring a light signal to deliver an amount of radiant exposure for a time. The configuring can be done by a controller. The configured light signal can be delivered to the certain area of the patient's brainstem by an optrode. The certain area of the patient's brainstem can include brainstem circuitry that acts as a control center for the cardiorespiratory response. In response to the amount of radiant exposure delivered to the specific area of the brainstem for the time, the cardiorespiratory response can be evoked in the patient.

In another aspect, the present disclosure can include a system that can be used to modulate neural function in a certain area of a patient's brainstem to evoke a cardiorespiratory response. The system can include a controller, a light generator, and an optrode. The controller can be configured to configure a light signal with an amount of radiant exposure to be delivered for a time. The light generator can be configured to receive the configuration from the controller and generate the light signal with the configuration. The optrode can be configured to be placed proximal to a portion of the patient's brainstem, which includes the certain area, and deliver the light signal to the portion of the patient's brainstem. Based on the delivery of the light signal, the certain area of the patient's brainstem can experience the radiant exposure to trigger the cardiorespiratory response.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Unless otherwise defined, all technical terms used herein have the same meaning as commonly understood by one of ordinary skill in the art to which the present disclosure pertains.

As used herein, the singular forms "a," "an" and "the" can also include the plural forms, unless the context clearly indicates otherwise.

As used herein, the terms "comprises" and/or "comprising," can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the terms "first," "second," etc. should not limit the elements being described by these terms. These terms are only used to distinguish one element from another. Thus, a "first" element discussed below could also be termed a "second" element without departing from the teachings of the present disclosure. The sequence of operations (or acts/ steps) is not limited to the order presented in the claims or figures unless specifically indicated otherwise.

As used herein, the term "neural modulation" or "neuromodulation" can refer to the alteration of nerve activity through targeted delivery of a stimulus to one or more specific neurological sites in a patient's body. The targeted delivery of the stimulus can be used for stimulation or inhibition of nerve activity.

As used herein, the term "conduction" can refer to the transmission of one or more action potentials.

As used herein, the term "inhibition" can refer to interference, with or restraint of, conduction. In other words, inhibition can be used to impede the transmission of action potentials.

As used herein, the term "threshold" can refer to a maximum or minimum change in intensity resulting in a functional result. For example, the functional result can be enhancing conduction or inhibiting conduction caused by application of a certain amount of stimulus.

As used herein, the term "light signal" can refer to any signal including electromagnetic radiation that can be used as a stimulus. An example of a light signal is an infrared (IR) light signal.

As used herein, the term "radiant exposure" can refer to an amount of radiant energy received by a surface per unit area (expressed in $J/cm^2/pulse$). Equivalently, the radiant exposure can be expressed as the irradiance that reaches a surface area due to irradiance, maintained for a particular duration of time.

As used herein, the term "target area" can refer to an area of a patient's nervous system selected to receive a stimulus for neuromodulation. In some instances, the target area can be a portion of the patient's brainstem chosen based on a desired response.

As used herein, the term "brainstem" can refer to the posterior part of the brain, continuous with the spinal cord. For example, the brainstem can include at least the midbrain and the pons and medulla oblongata (or medulla) of the hindbrain. Different portions of the brainstem can control different biological responses.

As used herein, the term "proximal" can refer to something being positioned close to something else. Although the term proximal may also encompass being on or within, something proximal need not be on or within.

As used herein, the term "subject" can refer to any warm-blooded organism including, but not limited to, a human being, a pig, a rat, a mouse, a bird, a dog, a cat, a goat, a sheep, a horse, a monkey, an ape, a rabbit, a cow, etc. The term "patient" can be used interchangeably with "subject".

II. Overview

The present disclosure relates to systems and methods for modulating neural activity in brainstem circuitry. The brainstem contains control circuitry for many bodily functions, including cardiorespiratory functions, like heart rate, blood pressure, and breathing. The brainstem is an easily accessible target for neuromodulation; however, traditional neuromodulation mechanisms, including electrical stimuli, cannot target specific brainstem circuitry. For example, an electrical stimulation intended to decrease a patient's heart rate may also, inadvertently, decrease the patient's breathing rate due to the fact that electrical stimulation cannot be spatially controlled. In contrast, a light signal, when used as the neuromodulation mechanism, can be easily controlled to provide high spatial selectivity without requiring contact with the brainstem, without the need for exogenous agents to be added to the tissue of the brainstem, without providing stimulation artifacts, and without causing tissue damage.

For example, neuromodulation of the brainstem with a light signal, such as an infrared (IR) light signal, evokes large cardiorespiratory response in a dose- and location-dependent manner. The light can be configured to deliver a certain dose (or amount of radiant exposure) to a specific portion of the brainstem for a time. The specific portion of the brainstem and/or the dose can be chosen based on the desired cardiorespiratory response. The configured light signal can be delivered to the specific portion of the patient's brainstem by an optrode such that the specific dose is delivered to the specific portion of the patient's brainstem. Based on the neuromodulation, the desired cardiorespiratory response can be evoked in the patient.

III. Systems

One aspect of the present disclosure can include a system 10 (FIG. 1) that can use a light signal to modulate neural activity in brainstem circuitry. Based on the radiant exposure delivered for the time to the specific area A significant benefit of using light (e.g., infrared (IR) light signal) compared to other neuromodulatory stimuli (e.g., an electrical signal or a magnetic signal) is spatial selectivity and precision of stimulation. In other words, using light to modulate a portion of a patient's brainstem can confine the neuromodulation to the specific portion of the patient's brainstem including certain brainstem circuitry to evoke a certain bodily function without evoking other unintended bodily functions. Additionally, stimulation with light does not require contact with the target area of stimulation (although the light can be delivered directly to the target area, the light need only be delivered proximal to the target area), stimulation with light does not create stimulation artifacts, and stimulation with light does not require exogenous agents to be added to the tissue being stimulated.

Figure 1:
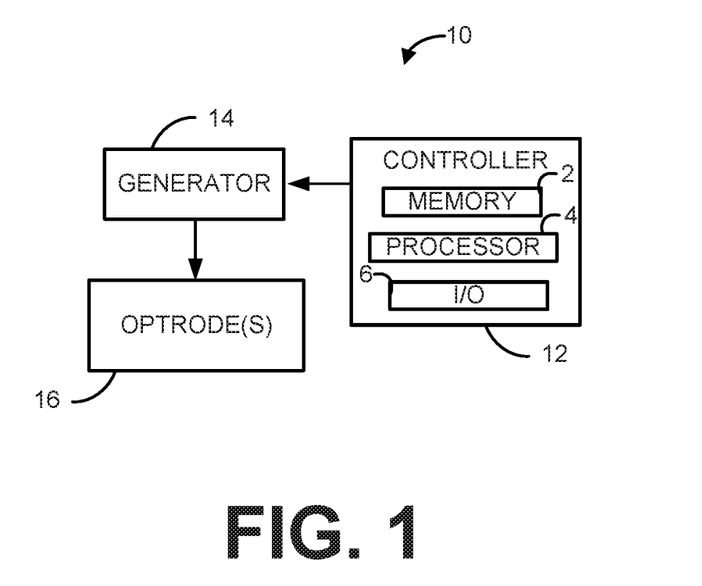
FIG. 1 is a diagram showing a system that can use light to modulate neural activity in brainstem circuitry in accordance with an aspect of the present disclosure.

The system 10 can include a controller 12, a generator 14, and one or more optrodes 16. The controller 12 can be coupled to the generator 14, which can be coupled to the one or more optrodes 16. In some instances, the coupling between the controller 12 and the generator 14 and/or the coupling between the generator 14 and the one or more optrodes 16 can be via a wired connection. In other instances, the coupling between the controller 12 and the generator 14 and/or the coupling between the generator 14 and the one or more optrodes 16 can be via a wireless connection. In still other instances, the coupling between the controller 12 and the generator 14 and/or the coupling between the generator 14 and the one or more optrodes 16 can be via a connection that is both wired and wireless. In some instances, at least a portion of the controller 12 and at least a portion of the generator 14 can be included within a single hardware device, but in other instances, the controller 12 and the generator 14 can be entirely distinct hardware devices. Additionally, each element of the system 10 may have additional components to aid in the coupling that are not illustrated.

The controller 12 can be configured to define parameters for a light signal. The parameters can include at least an amount of radiant exposure to be delivered for a time, which may be based on the target portion of the patient's brainstem to be stimulated. In response to the radiant exposure being applied to a certain location of the patient's brainstem, a certain bodily function can be evoked. The certain area of the patient's brainstem can include control circuitry for the certain bodily function. As an example, the certain area of the patient's brainstem can include the ponto-medullary ventrolateral cell column respiratory pattern generator or the rostral ventrolateral medulla sympathetic pattern generator and the certain bodily function can include one or more cardiorespiratory responses.

Figure 2:
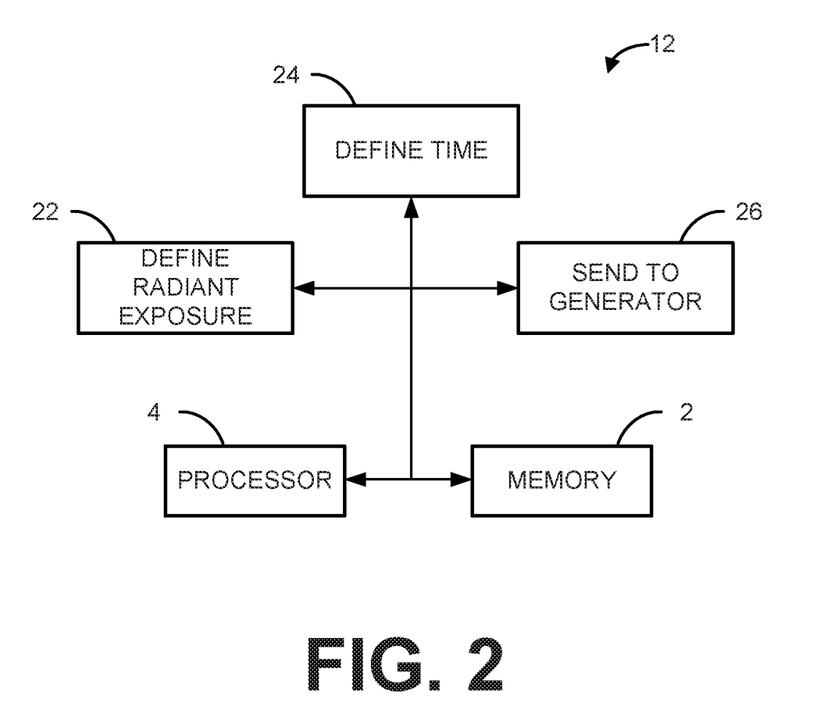
FIG. 2 is a diagram showing an example configuration of the controller in FIG. 1.

The controller 12 can include at least a non-transitory memory 2, a processor 4, and an input/output (I/O) 6. The non-transitory memory 2 can store machine executable instructions, which are executable by the processor 4 (for example, as shown in FIG. 2, the machine executable instructions can include define a radiant exposure to be delivered by the light 22, define a time for application of the light 24, and send the configuration to the generator 26). In some instances, the non-transitory memory 2 and the processor 4 can be combined in a single hardware element (e.g., a microprocessor), but in other instances, the non-transitory memory 2 and the processor 4 can include at least partially distinct hardware elements. The I/O 6 can provide an output that includes the configuration of the signal to the generator 14. In some instances, the I/O 6 can receive an input (e.g., based on a manual input, based on a predefined prescription, based on a property recorded by one or more sensors, or the like) that aids in the configuration of the light.

The generator 14 can be configured to receive the output from the controller 12 and generate the light with the specified configuration. The generator 14 can be any device configured or programmed to generate the specified light signal for application to the certain portion of the brainstem. For example, when the light signal is an IR light signal that includes one or more pulses of IR, the generator 14 can be an IR light source, like at least one IR laser and/or at least one IR emitting diode. It will be appreciated that the generator 14 can include additional components to selectively configure the light signal, such as a modulator (not shown).

The generator 14 can deliver the light signal to the one or more optrodes 16 for application to the certain portion of the patient's brainstem. For example, the generator 14 can be connected to the one or more optrodes 16 by a fiber optic cable (e.g., a flexible fiber optic cable made at least in part of a polymer material) to facilitate delivery of the light signal from the generator 14 to the one or more optrodes 16. The one or more optrodes 16 can be placed proximal to one or more portions of the patient's brainstem. In some instances, the one or more optrodes 16 can contact the one or more portions of the patient's brainstem. In other instances, the one or more optrodes 16 can be located close to the one or more portions of the patient's brainstem without contacting the patient's brainstem. The one or more optrodes 16 can deliver the light to the portion of the patient's brainstem.

IV. Methods

Figure 3:
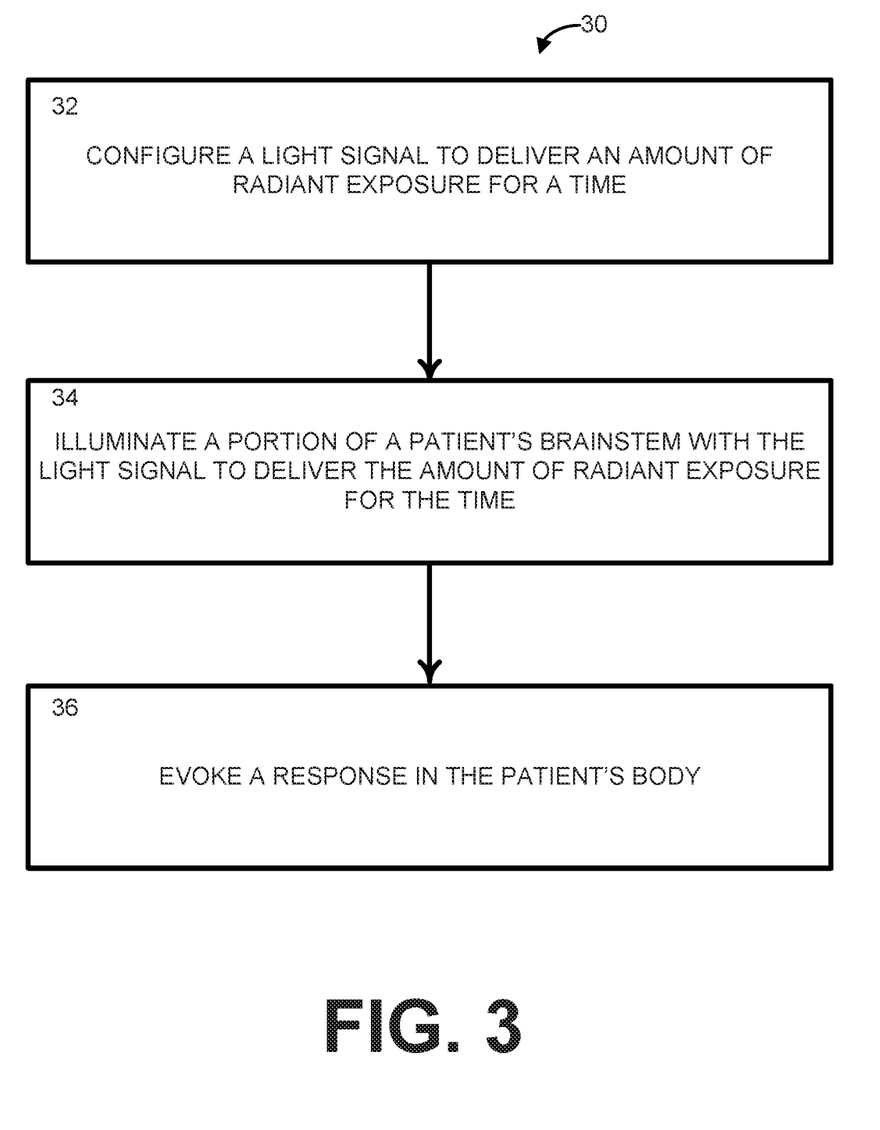
FIG. 3 is a process flow diagram illustrating a method for using light to modulate neural activity in brainstem circuitry according to another aspect of the present disclosure.

Another aspect of the present disclosure can include a method 30 for using a light signal to modulate neural activity in brainstem circuitry. The method 30 can be executed using at least a portion of the system 10 shown in FIGS. 1 and 2 and described above. The method 30 is illustrated as a process flow diagram with flowchart illustrations. For purposes of simplicity, the method 30 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 30.

At step 32, a light signal can be configured (e.g., by controller 12) to deliver an amount of radiant exposure for a time. The light signal can be configured to deliver an amount of radiant exposure for a time. In some instances, the amount of radiant exposure can be a near-threshold dose. In response to the near-threshold dose and the area of the patient's brainstem targeted, the bodily function can be at least one of a transient expiratory facilitation, a transient decrease in respiratory frequency, a transient increase in vagal nerve activity (VNA), a decrease in thoracic sympathetic nerve activity (tSNA), a decrease in perfusion pressure, and a decrease in heart rate. In other instances, the amount of radiant exposure can be a supra-threshold dose. In response to the supra-threshold dose and the area of the patient's brainstem targeted, the bodily function can be at least one of an inspiratory facilitation, an increase in respiratory frequency, a decrease in vagal nerve activity (VNA), a decrease in thoracic sympathetic nerve activity (tSNA), a decrease in perfusion pressure after the time, or a decrease in heart rate.

At step 34, a portion of a patient's brainstem can be stimulated (through one or more optrodes 16) with the light signal (generated by the generator 14) to deliver the amount of radiant exposure for the time. For example, the light signal can be an infrared (JR) light signal (e.g., including one or more pulses of IR light) delivered by an IR generator, such as one or more IR lasers or one or more IR emitting diodes, and delivered to one or more optrodes through a flexible fiber optic (e.g., including a polymer material). The portion of the patient's brainstem can include control circuitry for a bodily function. For example, the portion of the patient's brainstem comprises at least one of a calamus scriptorius (CS), an area postrema (AP), a fourth ventricle, and a nucleus tractus solitaries. At step 36, a response is evoked in the patient's body based on the stimulation of the portion of the brainstem with the light signal. For example, the response can be related to the bodily function that is triggered by the amount of radiant exposure applied for the time.

VII. Experimental

The following experiment shows that neuromodulation of the nucleus Tractus Solitarii (nTS) of a Sprague-Dawley rat with infrared (JR) light alters cardiorespiratory activity. The following experimental results are shown for the purpose of illustration only and are not intended to limit the scope of the appended claims.

Figure 4:
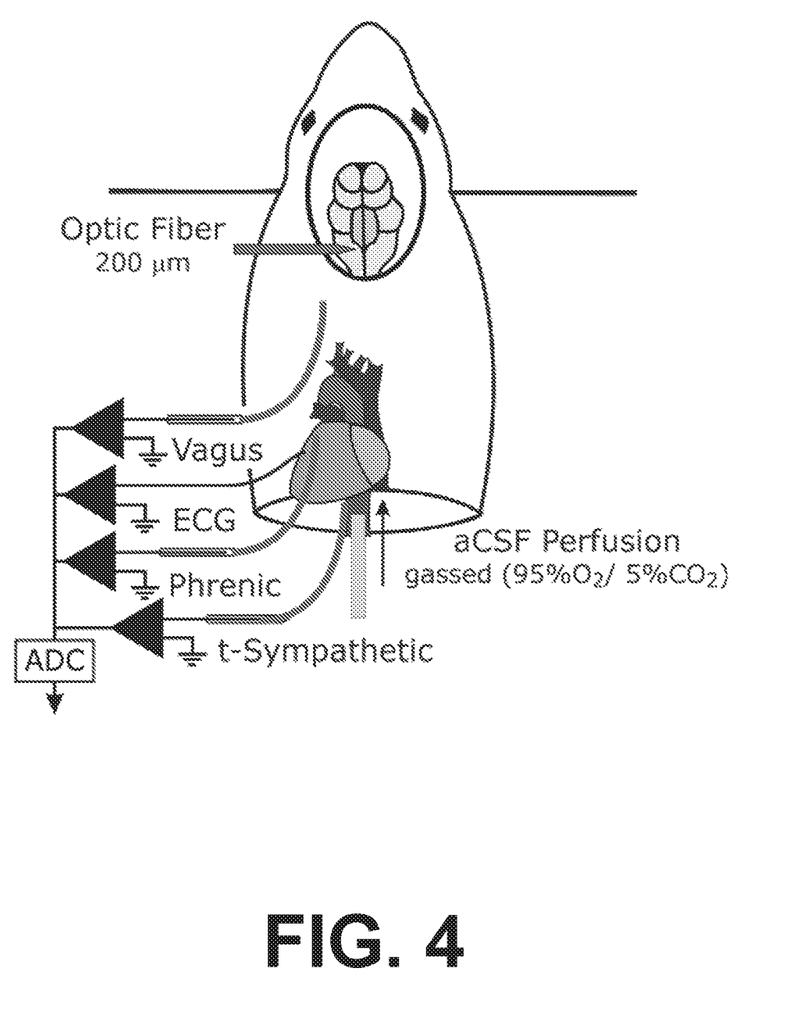
FIG. 4 shows an example experimental configuration.

Experimental Methods 10 male Sprague-Dawley rats were prepared according to the in-situ arterially perfused brain preparation shown in FIG. 4. Vagal (VNA), Phrenic (PNA), and thoracic Sympathetic (tSNA) nerve activities were recorded. Electrocardiogram (ECG) and perfusion pressure (PP) were also recorded. The IR diode laser used provided IR light with a wavelength of 1464 nm, a pulse duration of 200 ms, and a pulse frequency of 200 Hz. The IR diode laser sent the IR light through an optic fiber with a 200 nm diameter for delivery to the nTS.

The protocol included baseline recording (Bsin, 10 min), activate IR laser (30-s train of pulses applied to the nTS), recovery period (Rcvry, 5 min), repeating IR activation every 5 minutes with radiant exposure levels increased progressively.

Results

Figure 5A:
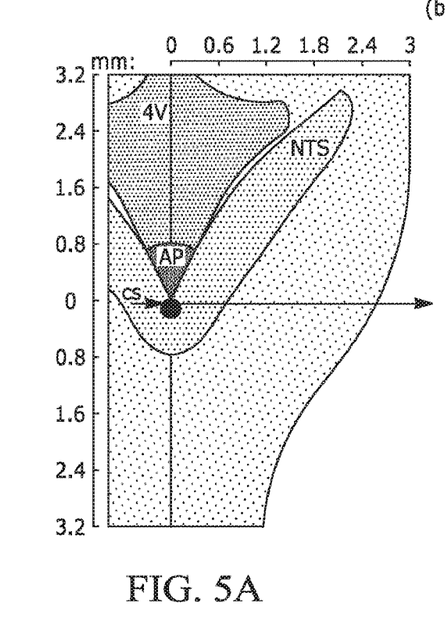
FIG. 5 shows how application of infrared (JR) light affects cardiorespiratory activity.
Figure 5B:
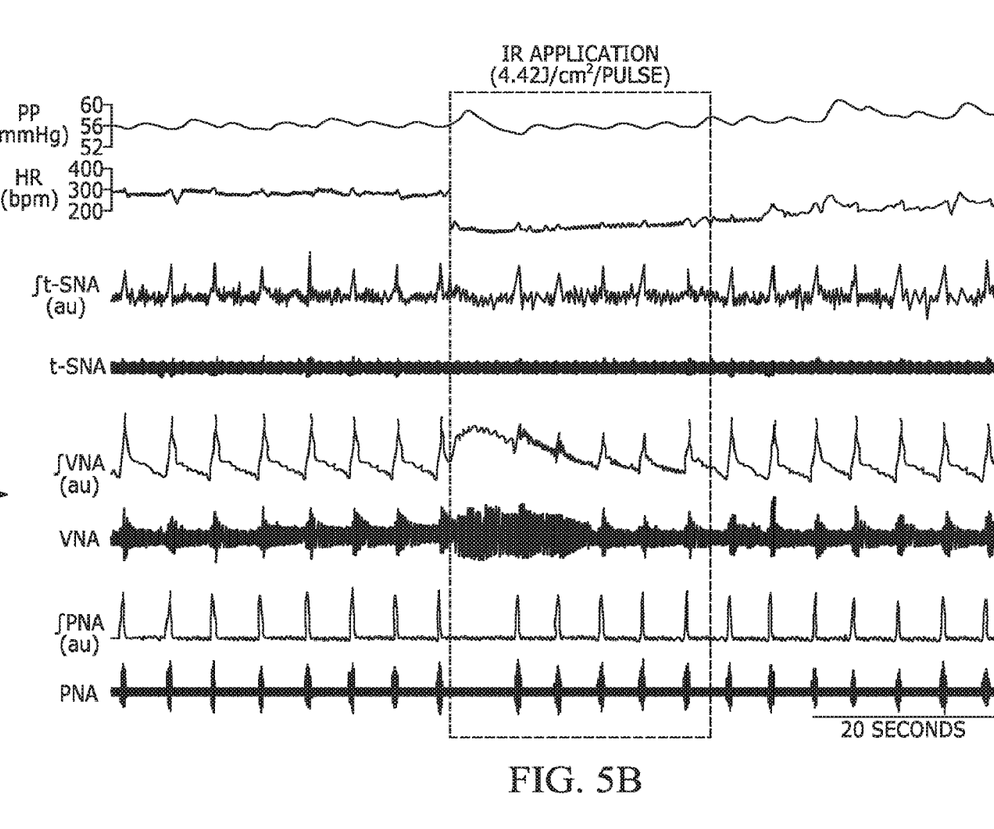

As shown in FIG. 5, IR light affects cardiorespiratory activity with a large cardiorespiratory response. The IR probe was placed proximal to the brainstem, as shown A (AP is the Area Postrema, Calif. is the Calamus Scriptorius, NTS is the nucleus Tractus Solitaries (NTS), 4V is the fourth ventricle). IR light was applied according to the protocol at 4.42 $J/cm^2$/pulse. As shown in B, application of the IR light had a noticeable effect on perfusion pressure (PP), heart rate (HR). In other words, the respiratory response was transient expiratory facilitatory, transient decrease in respiratory frequency. Other measurements of integrated thoracic sympathetic nerve activity, thoracic sympathetic nerve activity (t-SNA), integrated cervical vagal nerve activity, cervical vagal nerve activity (VNA), integrated phrenic nerve activity, and phrenic nerve activity (PNA). As shown, there was a transient increase in VNA, a decrease in tSNA, a decrease in PP, and a decrease in heart rate.

Figure 6:
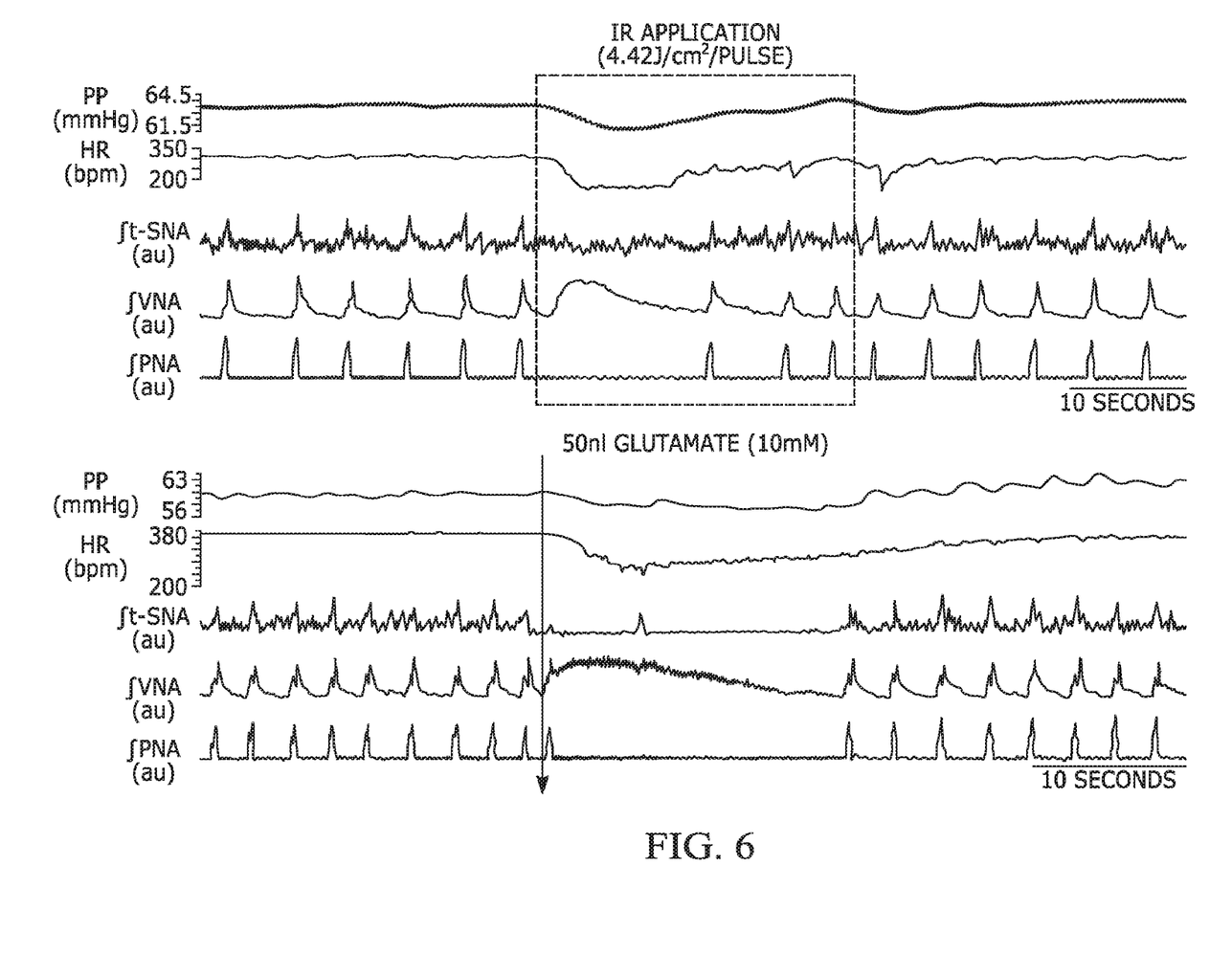
FIG. 6 shows how near-threshold IR light stimuli affects cardiorespiratory activity similar to glutamate microinjection.
Figure 7:
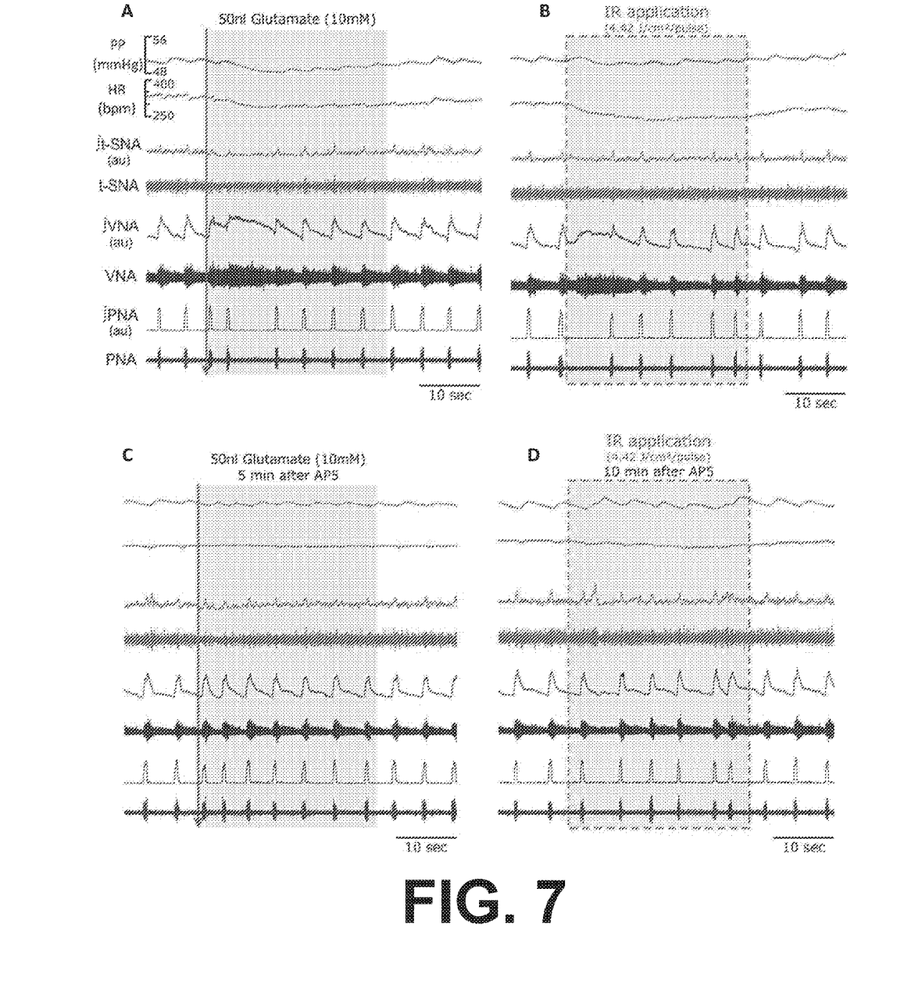
FIG. 7 shows how the glutamate blocker AP5 diminished the effect of subsequent IR application.

FIG. 6 shows that near-threshold IR light stimuli affects cardiorespiratory activity similar to glutamate microinjection. Results from IR being applied according to the protocol at 0.442 $J/cm^2$/pulse (top) and after administration of 50 nL of 10 mM glutamate (top) show a similar effect. As shown in FIG. 7, administration of a glutamate blocker (AP5) diminished the effect of subsequent IR application (A and B show the respective glutamate and IR effects on cardiorespiratory activity before AP5 microinjection, while C and D show respective glutamate and IR effect on cardiorespiratory activity being diminished after AP5 microinjection). Since the Glutamate blocker (AP5) microinjection on the cNTS diminished the effect of subsequent IR application, perhaps near-threshold IR activates $TRPV_{1\&4}$.

Figure 8:
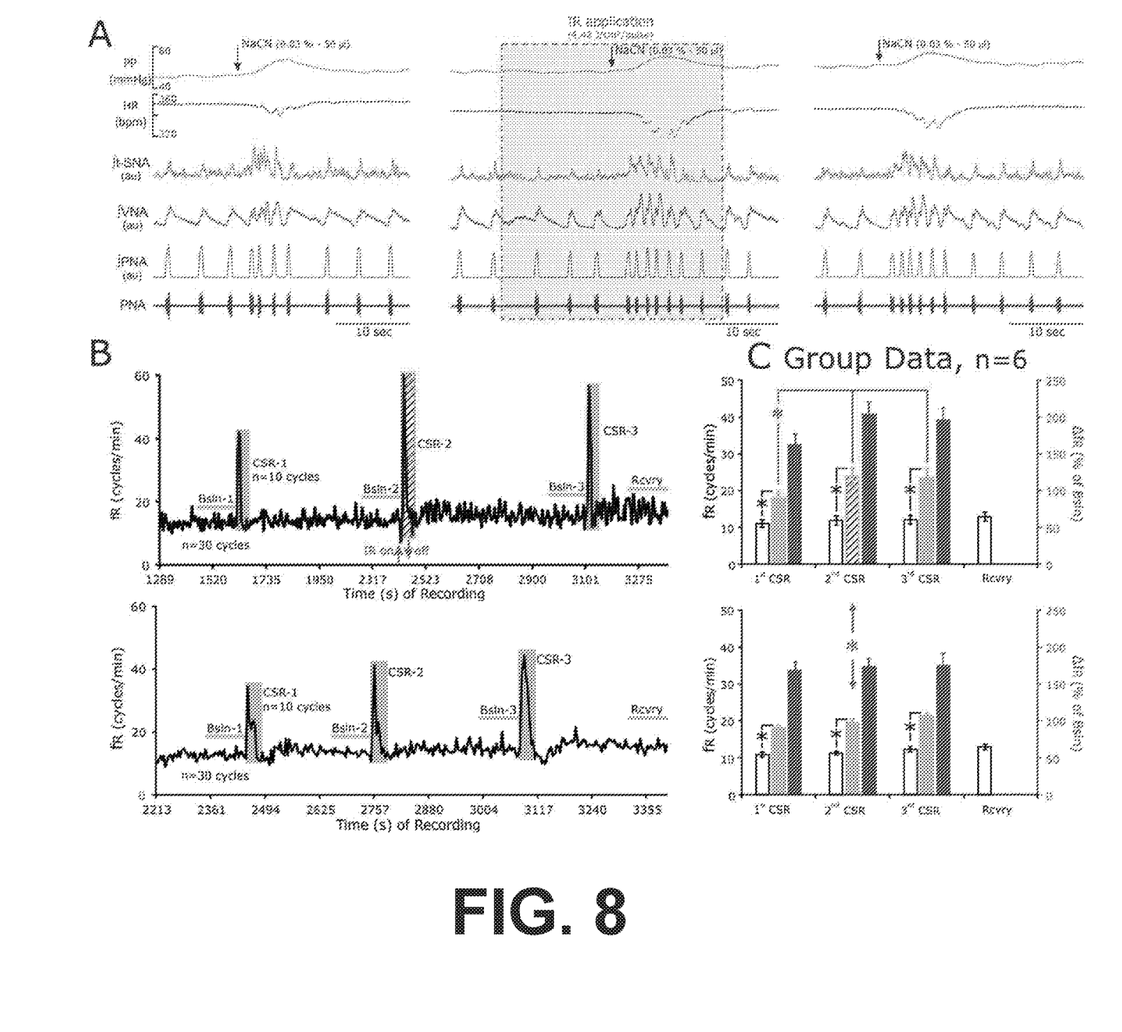
FIG. 8 shows that IR light accentuated chemo-reflex responses.

FIG. 8 shows how IR light accentuated chemo-reflex responses. Representative traces of responses to NaCN are shown in A. Before (left), during (center) and after (right) IR exposure. Instantaneous fR for IR exposure is shown in B based on the raw data (top) and control (bottom). Group data is shown in C. The chemo-reflex response (CSR) to NaCN (0.03%, 50 μL increased during IR application. For the IR group, the actual and percent increase in fR of the second CSR were greater than the first CSR of the control group (arrows). The third CSR was also greater after IR activation, which indicates a persistence of the IR effect.

Figure 9:
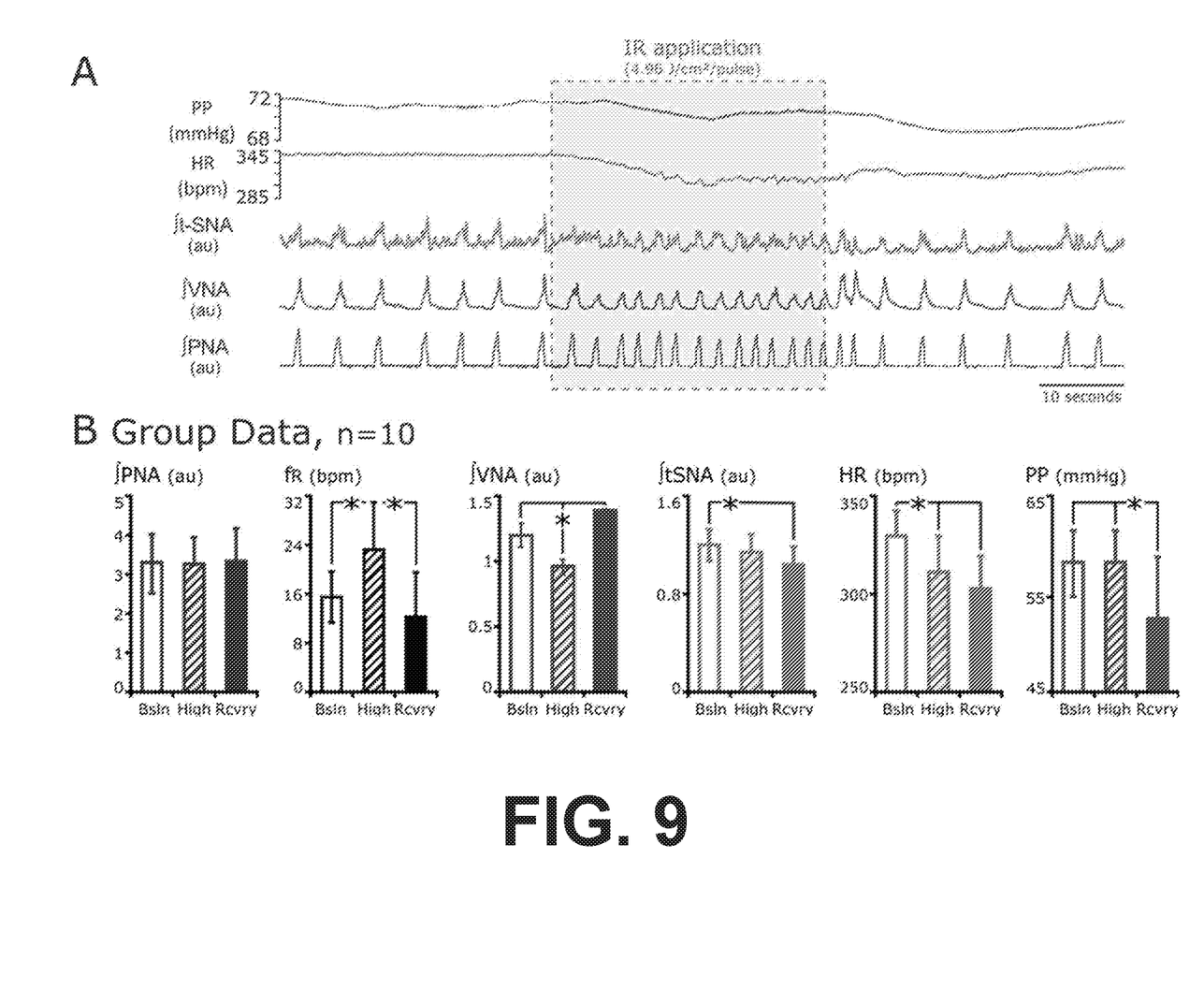
FIG. 9 shows how IR light at supra-threshold radiant exposure levels exhibits differential effects on cardiorespiratory activity.

FIG. 9 shows that IR light at supra-threshold radiant exposure levels has differential effects on cardiorespiratory activity. The respiratory response is inspiratory facilitatory with an increase in respiratory frequency. A decrease in VNA, a decrease in tSNA, a decrease in PP, which is greater once the IR light was turned off. The cardiac response is a decrease in heart rate.

Figure 10:
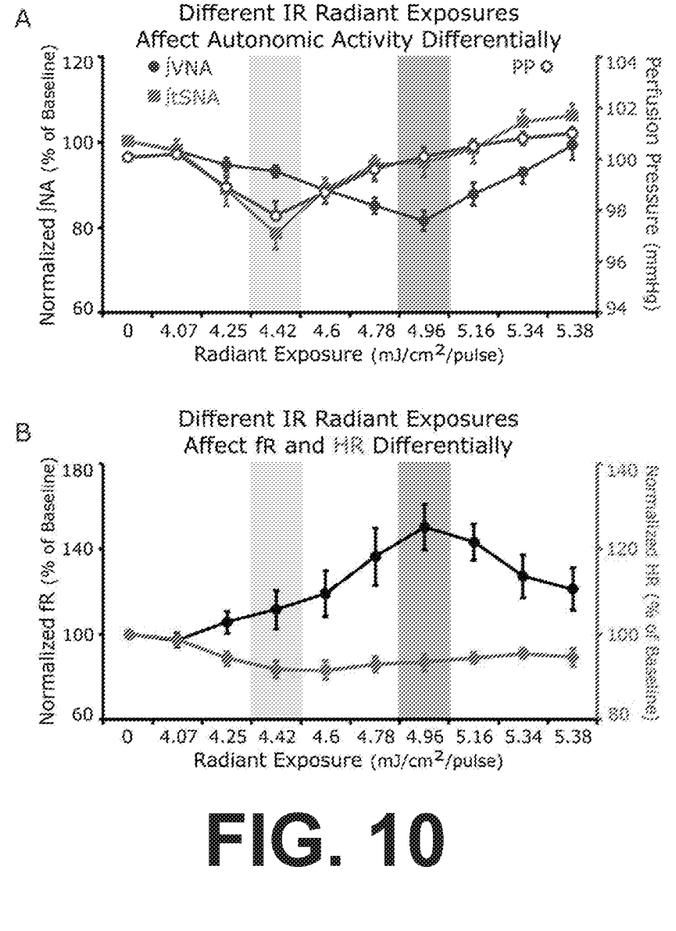
FIG. 10 shows how IR light has a dose-dependent effect on cardiorespiratory activity.
Figure 11:
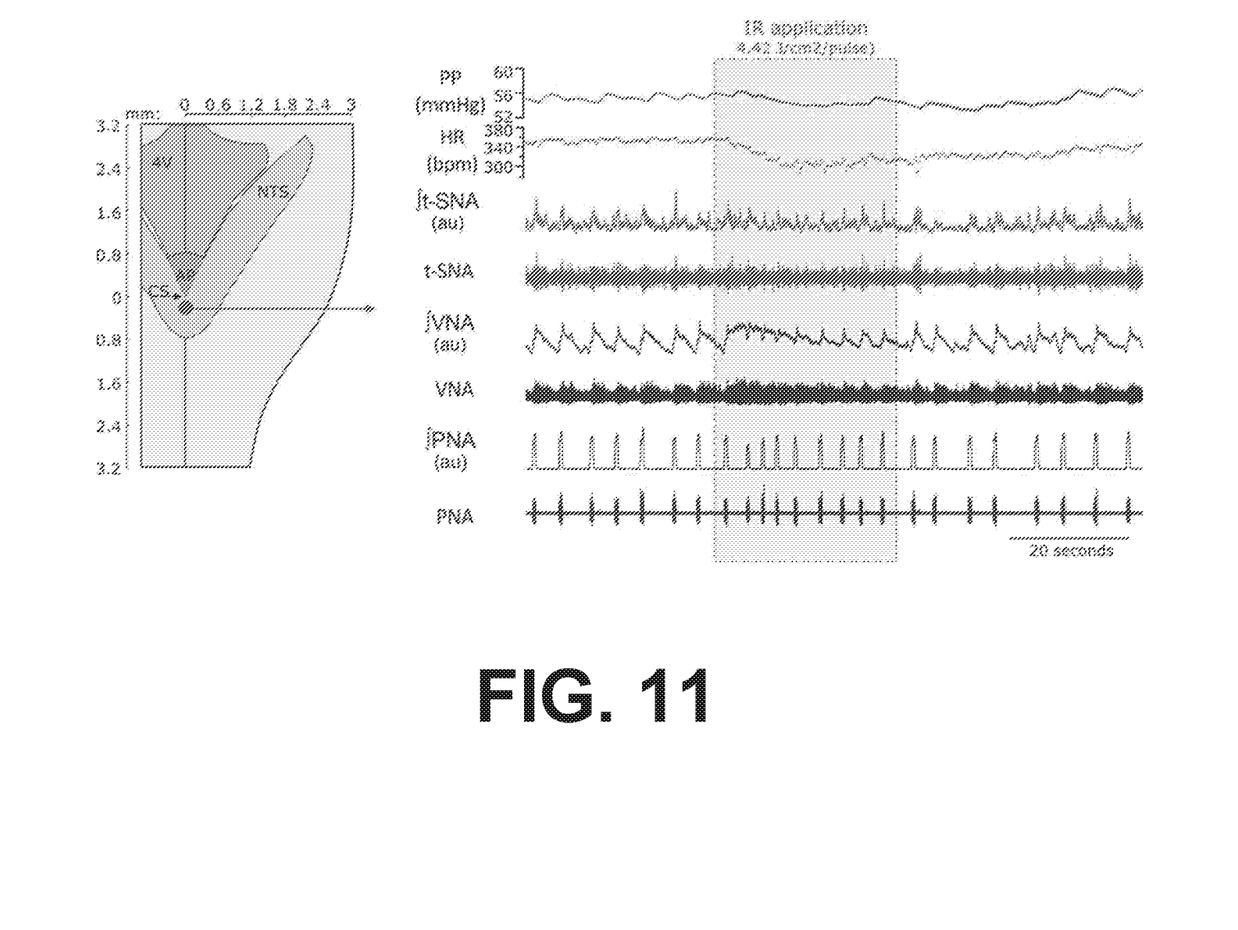
FIGS. 11 and 12 show how IR light has a site-dependent effect on cardiorespiratory activity.
Figure 12:
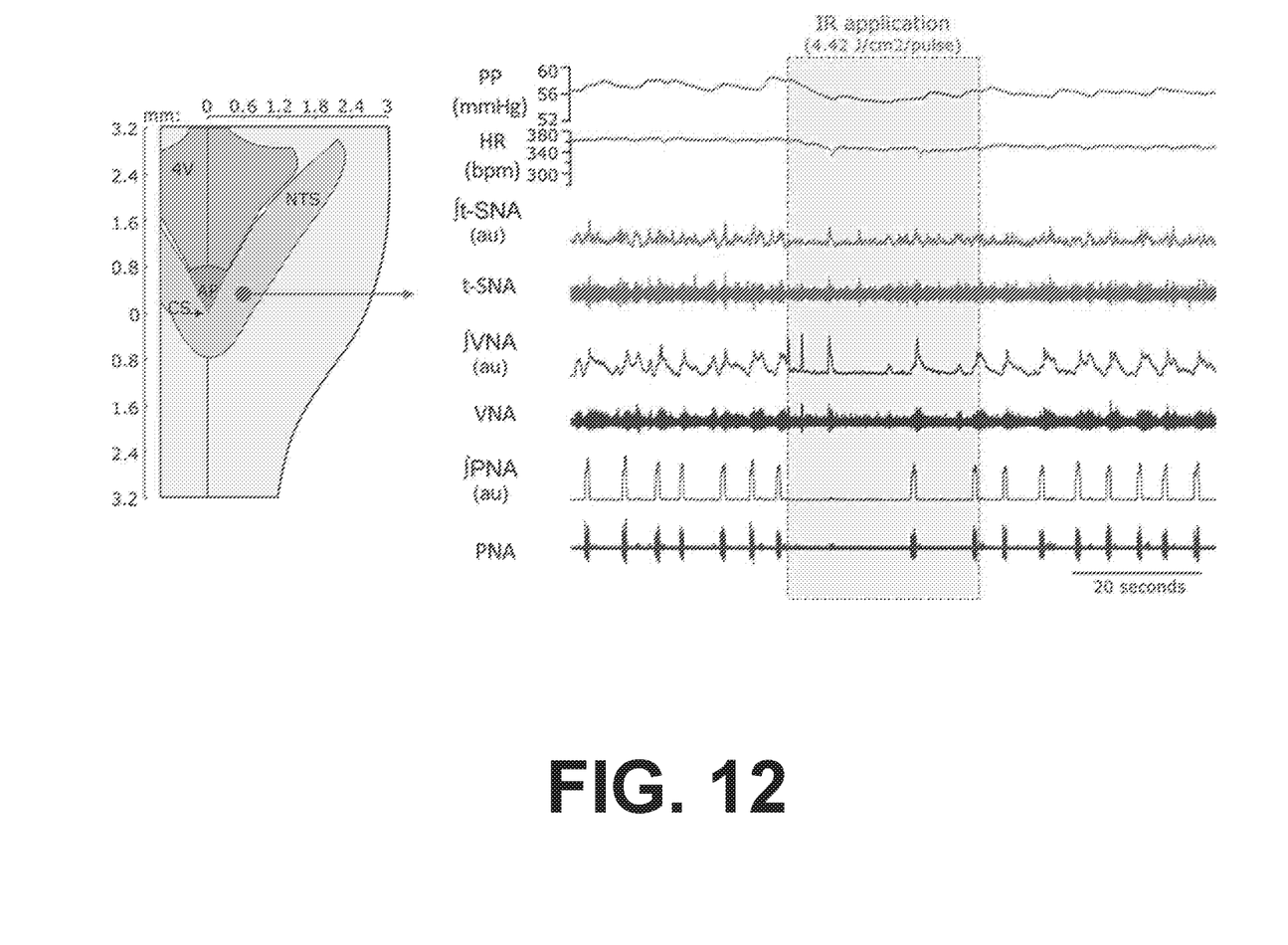

IR light affects cardiorespiratory activity in a dose- and location-dependent manner. FIG. 10 shows how IR light has a dose-dependent effect on cardiorespiratory activity. The cardiorespiratory responses to IR activation depend on radiant exposure levels—light grey box is the response to near-threshold radiant exposure, while the darker grey box is the response to supra-threshold exposure. Close to threshold radiant exposure of IR light (light grey box) decreased the integral of tSNA and PP. Supra-threshold radiant exposure of IR light (dark grey box) decreased the integral of VNA and respiratory frequency (fR). Heart rate (HR) decreased at near threshold radiant exposure as the integral of tSNA initially. At supra-threshold radiant exposure levels, HR decreased, but the average amplitude of the integral of tSNA returned towards the baseline. At higher radiant exposure levels of IR, the effects on cardiorespiratory variables decreased. The effects of IR light at threshold and supra-threshold are reversible, which indicates that these levels of IR do not damage the tissue. FIGS. 11 and 12 illustrate how IR light has a site-dependent effect on cardiorespiratory activity. As shown in FIG. 11, the IR probe placed 100-200 m caudal to the Calamus Scriptorius changes cardiorespiratory activity differently than the IR probe placed 300 m rostral to the Calamus Scriptorius and 600 m lateral to the midline.

From the above description, those skilled in the art will perceive improvements, changes and modifications. Such improvements, changes and modifications are within the skill of one in the art and are intended to be covered by the appended claims.

The following is claimed:

1. A method comprising:
   selecting, by a controller, parameters of an infrared (IR) light signal to evoke a cardiorespiratory response in a patient, wherein the parameters comprise an amount of radiant exposure and a time for delivery;
   generating, by a light generator, the IR light signal based on the parameters; and
   stimulating, by an optrode, a nucleus Tractus Solitarii of the patient with the IR light signal, comprising thirty second repeating intervals of IR light pulses with five-minute recovery periods between the intervals, to evoke the cardiorespiratory response, wherein the optrode is configured to be placed proximal to the patient's nucleus Tractus Solitarii.

2. The method of claim 1, wherein the amount of radiant exposure corresponds to a near-threshold dose of the IR light signal.

3. The method of claim 2, wherein the cardiorespiratory response comprises at least one of a transient expiratory facilitation, a transient decrease in respiratory frequency, a transient increase in vagal nerve activity (VNA), a decrease in thoracic sympathetic nerve activity (tSNA), a decrease in perfusion pressure, and a decrease in heart rate.

4. The method of claim 1, wherein the amount of radiant exposure corresponds to a supra-threshold dose of the IR light signal.

5. The method of claim 4, wherein the cardiorespiratory response comprises at least one of an inspiratory facilitation, an increase in respiratory frequency, a decrease in vagal nerve activity (VNA), a decrease in thoracic sympathetic nerve activity (tSNA), a decrease in perfusion pressure after the time, or a decrease in heart rate.

6. The method of claim 1, wherein the IR light signal comprises a plurality of IR laser pulses.

7. The method of claim 1, wherein the optrode is positioned to contact the patient's nucleus Tractus Solitarii.

8. The method of claim 1, wherein the IR light is configured to have a pulse duration of 200 ms and a pulse frequency of 200 Hz.

9. The method of claim 1, wherein the IR light is applied at 4.42 $J/cm^2$/pulse.

10. A system comprising:
    a controller configured to select parameters of an infrared (IR) light signal to evoke a cardiorespiratory response in a patient, wherein the parameters comprise an amount of radiant exposure and a time for delivery;
    a light generator comprising at least one IR light source configured to receive the parameters from the controller and generate the IR light signal with the parameters, wherein the light signal comprises thirty second repeating intervals of IR light pulses with five-minute recovery periods between the intervals; and an optrode configured to be placed proximal to the patient's nucleus Tractus Solitarii and deliver the IR light signal to the patient's nucleus Tractus Solitarii with the amount of radiant exposure for the time to evoke the cardiorespiratory response.

11. The system of claim 10, wherein the at least one IR light source comprises at least one of an IR laser or an IR emitting diode.

12. The system of claim 10, wherein the IR light signal comprises a plurality of IR laser pulses.

13. The system of claim 10, further comprising a flexible fiber optic cable linking the light generator to the optrode, wherein the flexible fiber optic cable comprises a polymer material.

14. The system of claim 10, wherein the optrode is configured to contact the patient's nucleus Tractus Solitarii.

15. The system of claim 10, wherein the IR light is configured to have a pulse duration of 200 ms and a pulse frequency of 200 Hz.

16. The system of claim 10, wherein the light generator generates the IR light signal at 4.42 $J/cm^2$/pulse.

* * * * *